United States Patent
Santti et al.

(10) Patent No.: US 8,962,693 B2
(45) Date of Patent: Feb. 24, 2015

(54) METHOD FOR THE TREATMENT OR PREVENTION OF LOWER URINARY TRACT SYMPTOMS

(71) Applicant: Hormos Medical Corporation, Turku (FI)

(72) Inventors: Risto Santti, Naantali (FI); Tomi Streng, Turku (FI)

(73) Assignee: Hormos Medical Ltd., Turku (FI)

( * ) Notice: Subject to any disclaimer, the term of this patent is extended or adjusted under 35 U.S.C. 154(b) by 0 days.

(21) Appl. No.: 13/970,026

(22) Filed: Aug. 19, 2013

(65) Prior Publication Data

US 2013/0345313 A1 Dec. 26, 2013

Related U.S. Application Data

(63) Continuation of application No. 12/856,738, filed on Aug. 16, 2010, now abandoned, which is a continuation of application No. 10/454,823, filed on Jun. 5, 2003, now abandoned.

(51) Int. Cl.

| | | |
|---|---|---|
| *A01N 31/14* | (2006.01) | |
| *A61K 31/075* | (2006.01) | |
| *A01N 31/00* | (2006.01) | |
| *A61K 31/045* | (2006.01) | |
| *A61K 31/085* | (2006.01) | |
| *A61K 31/00* | (2006.01) | |
| *A61K 31/138* | (2006.01) | |
| *A61K 31/192* | (2006.01) | |
| *A61K 31/40* | (2006.01) | |
| *A61K 31/404* | (2006.01) | |
| *A61K 31/4045* | (2006.01) | |
| *A61K 31/4164* | (2006.01) | |
| *A61K 31/453* | (2006.01) | |
| *A61K 31/4535* | (2006.01) | |
| *A61K 31/454* | (2006.01) | |
| *A61K 31/55* | (2006.01) | |
| *A61K 31/565* | (2006.01) | |

(52) U.S. Cl.
CPC .............. *A61K 31/085* (2013.01); *A61K 31/00* (2013.01); *A61K 31/138* (2013.01); *A61K 31/192* (2013.01); *A61K 31/40* (2013.01); *A61K 31/404* (2013.01); *A61K 31/4045* (2013.01); *A61K 31/4164* (2013.01); *A61K 31/453* (2013.01); *A61K 31/4535* (2013.01); *A61K 31/454* (2013.01); *A61K 31/55* (2013.01); *A61K 31/565* (2013.01)
USPC ........... 514/715; 514/717; 514/718; 514/721; 514/724

(58) Field of Classification Search
CPC ....... A61K 31/01; A61K 31/02; A61K 31/03; A61K 31/045; A61K 31/05; A61K 31/075; A61K 31/085
USPC .................. 514/651, 715, 717, 718, 721, 724
See application file for complete search history.

(56) References Cited

U.S. PATENT DOCUMENTS

| | | |
|---|---|---|
| 4,536,516 A | 8/1985 | Harper et al. |
| 4,656,187 A | 4/1987 | Black et al. |
| 4,696,949 A | 9/1987 | Toivola et al. |
| 4,839,155 A | 6/1989 | McCague |
| 4,894,373 A | 1/1990 | Young |
| 4,977,906 A | 12/1990 | Di Scipio |
| 4,996,225 A | 2/1991 | Toivola et al. |
| 5,118,667 A | 6/1992 | Adams et al. |
| 5,189,212 A | 2/1993 | Ruenitz |
| 5,192,525 A | 3/1993 | Yang et al. |
| 5,196,435 A | 3/1993 | Clemens et al. |
| 5,446,203 A | 8/1995 | McNelis |
| 5,470,883 A | 11/1995 | Stromberg |
| 5,491,173 A | 2/1996 | Toivola et al. |
| 5,658,931 A | 8/1997 | Bryant et al. |
| 5,691,355 A | 11/1997 | Bryant et al. |
| 5,693,674 A | 12/1997 | Bitonti |
| 5,703,109 A | 12/1997 | Karjalainen et al. |
| 5,719,136 A | 2/1998 | Chwalisz et al. |
| 5,750,576 A | 5/1998 | DeGregorio et al. |
| 5,807,899 A | 9/1998 | Bohlmann et al. |
| 5,821,254 A | 10/1998 | Sporn et al. |
| 5,827,892 A | 10/1998 | Löser et al. |
| 5,852,059 A | 12/1998 | Thompson |
| 5,861,389 A | 1/1999 | Radlmaier et al. |
| 5,877,219 A | 3/1999 | Willson |
| 5,912,273 A | 6/1999 | Degregorio et al. |

(Continued)

FOREIGN PATENT DOCUMENTS

| | | |
|---|---|---|
| CA | 2 430 769 | 6/2002 |
| EP | 0 095 875 A2 | 12/1983 |

(Continued)

OTHER PUBLICATIONS

Bentrem, D.J., et al., "Tamoxifen, raloxifene and the prevention of breast cancer", Minerva Endocrinologica, vol. 27, No. 2, 2002, pp. 127-139.
Budavari, S. et al., eds., *The Merck Index*, Eleventh Edition, p. 1430, No. 9019, Merck & Co., Inc., Rathway, NJ, USA (1989).
Budavari, S. et al., eds., *The Merck Index*, Eleventh Edition, p. 1433, No. 9039, Merck & Co., Inc., Rathway, NJ, USA (1989).
de Lignieres, B., "Transdermal Dihydrotestosterone Treatment of Andropause," 25 *Ann Med* 235-241 (1993).
Doran, P.M., "Effects of Raloxifene, a Selective Estrogen Receptor Modulator, on Bone Turnover Markers and Serum Sex Steroid and Lipid Levels in Elderly Men", Journal of Bone and Mineral Research, vol. 16, No. 11, 2001, pp. 2118-2125.

(Continued)

*Primary Examiner* — Yong Chong
(74) *Attorney, Agent, or Firm* — Brinks Gilson & Lione (57) ABSTRACT

This invention concerns a method for treatment or prevention of lower urinary tract symptoms with or without pelvic pain in an individual, said method comprising administering to the individual an effective amount of a selective estrogen receptor modulator, or an isomer, isomer mixture or a pharmaceutically acceptable salt thereof.

8 Claims, 4 Drawing Sheets

(56) References Cited

U.S. PATENT DOCUMENTS

| | | | |
|---|---|---|---|
| 5,972,921 | A | 10/1999 | Santti et al. |
| 6,037,379 | A | 3/2000 | Härkönen et al. |
| 6,262,115 | B1 | 7/2001 | Guittard et al. |
| 6,316,431 | B1 | 11/2001 | Santti et al. |
| 6,576,645 | B1 | 6/2003 | Södervall et al. |
| 6,608,111 | B1 | 8/2003 | Meyers et al. |
| 6,686,351 | B2 | 2/2004 | Bhagwat |
| 6,875,775 | B2 | 4/2005 | Södervall et al. |
| 7,825,107 | B2 | 11/2010 | Santti et al. |
| 2003/0036566 | A1 | 2/2003 | Blom et al. |

FOREIGN PATENT DOCUMENTS

| | | |
|---|---|---|
| EP | 0 779 808 B1 | 8/1999 |
| EP | 1 004 306 A2 | 5/2000 |
| EP | 1 199 069 A2 | 4/2002 |
| GB | 1064629 | 4/1967 |
| JP | 2000/503991 | 4/2000 |
| JP | 2001/502302 | 2/2001 |
| JP | 2002/508322 | 3/2002 |
| JP | 2002/179593 | 6/2002 |
| JP | 2003/514786 | 4/2003 |
| WO | WO 92/06068 | 4/1992 |
| WO | WO 93/19746 | 10/1993 |
| WO | WO 94/13645 | 6/1994 |
| WO | WO 95/26720 | 10/1995 |
| WO | WO 96/07402 | 3/1996 |
| WO | WO 96/09057 A1 | 3/1996 |
| WO | WO 96/21656 A1 | 7/1996 |
| WO | WO 96/35417 | 11/1996 |
| WO | WO 96/40616 A1 | 12/1996 |
| WO | WO 97/26876 | 7/1997 |
| WO | WO 97/32574 | 9/1997 |
| WO | WO 98/11888 | 3/1998 |
| WO | WO 99/30708 A2 | 6/1999 |
| WO | WO 99/42427 | 8/1999 |
| WO | WO 99/63974 | 12/1999 |
| WO | WO 00/55137 A1 | 9/2000 |
| WO | WO 01/36360 A1 | 5/2001 |
| WO | WO 01/97811 A1 | 12/2001 |
| WO | WO 02/03989 A2 | 1/2002 |
| WO | WO 02/090305 A1 | 11/2002 |
| WO | WO 03/039524 A1 | 5/2003 |
| WO | 2004/000801 A2 | 12/2003 |
| WO | WO 2004/108645 A1 | 12/2004 |

OTHER PUBLICATIONS

Gingell, J.G., et al., "Placebo Controlled Double-Blind Study to Test the Efficacy of the Aromatase Inhibitor Atamestane in Patients with Benign Prostatic Hyperplasia not Requiring Operation," *J. Urol.* 154:399-401 (Aug. 1995).

Glass, A.R., MD "Gynecomastia," 23 *Clinical Andrology* 825-837 (Dec. 1994).

Goldstein, S.R. et al., "A pharmacological review of selective oestrogen receptor modulators," *Human Reproduction Update* 6:212-224, Oxford University Press (May-Jun. 2000).

Grodstein, F. and Stampfer, M.J., "Estrogen for women at varying risk of coronary disease," *Maturitas* 30:19-26, Elsevier Science Ireland Ltd. (1998).

Hakenberg, O.W., et al., "Chronic Pelvic Pain in Men," *Urol. Intl.* 68:138-143 (2002).

Harkonen et al., "Role of estrogens in development of prostate cancer", *The Journal of Steroid Biochemistry & Molecular Biology*, 2004; 92:297-305.

Henderson, V.W., "Estrogen, Cognition, and a Woman's Risk of Alzheimer's Disease," *The American Journal of Medicine* 103:115-185, Excerpta Medica, Inc. (1997).

International Search Report for International Application No. PCT/FI00/00946, mailed Feb. 8, 2001.

International Search Report for International Application No. PCT/FI2004/000270, mailed Oct. 5, 2004.

International Preliminary Report on Patentability for International Application No. PCT/FI2004/000270, mailed Dec. 8, 2005.

Jordan, V.C., "Antiestrogens and Selective Estrogen Receptor Modulators as Multifunctional Medicines. 2. Clinical Considerations and New Agents," *J. Med. Chem.* 46(7):1081-1111 (Mar. 2003).

Kangas, L. et al., "A new triphenylethylene compound, Fc-1157a: II. Anti effects," *Cancer Chemother. Pharmacol.* 17:109-113, Springer-Verlag (1986).

Kangas, L. et al., "Bioluminescence of Cellular ATP: A New Method for Evaluating Cytotoxic Agents In Vitro," *Medical Biology* 62:338-343, Duodecim (1984).

Kangas, L., "Biochemical and Pharmacological Effects of Toremifene Metabolites," *Cancer Chemo. Pharmacol.* 27:8-12 (Apr. 1990).

Karjalainen, A. et al. (2000). "Synthesis of new potent and selective aromatase inhibitors based on long-chained diarylalkylimidazole and diarylalkyltriazole molecule skeletons," *Eur. J. Pharm. Sci.* 11:109-131.

Khovidhunkit, W. and Shoback, D.M., "Clinical Effects of Raloxifene Hydrochloride in Women," *Ann. Intern. Med.* 130:431-439, American College of Physicians (Mar. 1999).

Licata, A.A., et al., "Raloxifene: A new choice for treating and preventing osteoporosis", Osteoporosis Update reprinted from Cleveland Clinic Journal of Medicine, vol. 67, No. 4, Apr. 2000, pp. 273-280, reprinted as pp. 19-26.

Lobo, R.A., "Benefits and risks and estrogen replacement therapy," *Am. J. Obstet. Gynecol.* 173:982-989, Mosby-Year Book, Inc. (1995).

Macgregor, J.I. and Jordan, V.C., "Basic Guide to the Mechanisms of Antiestrogen Action," *Pharmacol. Rev.* 50:151-196, Williams and Wilkins Co. (1998).

Oesterling, J.E. et al. (1988) "Aromatase Inhibition in the DOG. II. Effect on Growth, Function, and Pathology of the Prostate", The Journal of Urology, vol. 139 Apr.:832-839.

Peng, Z. et al., "The Mechanical Strength of Bone in Different Rat Models of Experimental Osteoporosis," *Bone* 15:523-532, Elsevier Science Ltd. (1994).

Plouffe, L., "Selective Estrogen Receptor Modulators (SERMs) in Clinical Practice," *J. Soc. Gynecol. Investig.* 7:S38-S46, Elsevier Science Inc. (Jan.-Feb. 2000).

Qu, Q. et al., "Selective Estrogenic Effects of a Novel Triphenylethylene Compound, FC1271a, on Bone, Cholesterol Level, and Reproductive Tissues in Intact and Ovariectomized Rats," *Endocrinology* 14:809-820, Association for the Study of Internal Secretions (Fed. 2000).

Radlmaier A. et al., "Estrogen Reduction by Aromatase Inhibition for Benign Prostatic Hyperplasia: Results of a Double-Blind, Placebo-Controlled, Randomized Clinical Trial Using Two Doses of the Aromatase-Inhibitor Atamestane," *The Prostate* 29:199-208 (1996).

Renaud, J., et al., "Estrogen Receptor Modulators: Identification and Structure—Activity Relationships of Potent Erα-Selective Tetrahydroisoquinoline Ligands", J. Med. Chem., vol. 46, 2003, pp. 2945-2957.

Robinson, D., et al., "Overactive Bladder in the Female Patient: The Role of Estrogens", Current Urology Reports, vol. 3, 2002, pp. 452-457.

Robinson, D., et al., "The Role of Estrogens in Female Lower Urinary Tract Dysfunction", Urology, vol. 62, Supp. 4A, Oct. 2003, pp. 45-50.

Schilcher, H., "Miktionsbeeinflussende Mittel zur Behandlung der BPH," *Phytotherapie in der Urologie* 69-93 (1992).

Shuk-Mei Ho, "Estrogens and Anti-Estrogens: Key Mediators and Prostate Carcinogenesis and New Therapeutic Candidates", Journal of Cellular Biochemistry, vol. 91, 2004, pp. 491-503.

Simberg, N. H. et al., "In Vitro and In Vitro Binding of Toremifene and Its Metabolites in Rat Uterus," *J. Steroid Biochem.* 36:197-202, Pergamon Press: plc (1990).

Smetnik V.P. "Postmenopausal Disorders and Methods for Correcting Thereof"; Consilium-Medicum, 2001, No. 11, vol. 3; pp. 1-4; 14.

(56) References Cited

OTHER PUBLICATIONS

Smetnik V.P. "Postmenopausal Disorders and Methods for Correcting Thereof"; Consilium-Medicum, 2001, No. 11, vol. 3; (copy of Translation-pp. 1-3).

Steiner, M.S., et al., "Selection Estrogen Receptor Modulators for the Chemoprevention of Prostate Cancer", Urology, vol. 57, Supp. 4A, Apr. 2001, pp. 68-72.

Terenius, L., "Structure-Activity Relationships of Anti-Ostrogens With Regard to Interaction With 17β-Oestradiol in the Mouse Uterus and Vargina," *Acta Endocrinol.* 66:431-447, Scandinavian University Press (1971).

Usman Azam et al., "Economics of Lower Urinary Tract Symptoms (LUTS) in Older People", Drugs and Aging, vol. 18(3), 2001, pp. 214-223.

Yue, et al.; "Selective Estrogen Receptor Modulator Idoxifene Inhibits Smooth Muscle Cell Proliferation, Enhances Reendothelialization, and Inhibits Neointimal Formation In Vivo After Vascular Injury"; Departments of Cardiovascular Pharmacology and Experimental Toxicology; pp. III-281-III-288; Nov. 7, 2000.

METHOD FOR THE TREATMENT OR PREVENTION OF LOWER URINARY TRACT SYMPTOMS

CROSS-REFERENCE TO RELATED APPLICATIONS

This application is a continuation of U.S. patent application Ser. No. 12/856,738, filed on Aug. 16, 2010, which is a continuation of U.S. patent application Ser. No. 10/454,823, filed on Jun. 5, 2003, both of which are incorporated by reference in their entirety.

FIELD OF THE INVENTION

This invention relates to a method for treatment or prevention of lower urinary tract symptoms with or without pelvic pain in an individual, said method comprising administering to the individual an effective amount of a selective estrogen receptor modulator (SERM).

BACKGROUND OF THE INVENTION

The publications and other materials used herein to illuminate the background of the invention, and in particular, cases to provide additional details respecting the practice, are incorporated by reference.

Lower Urinary Tract Symptoms (LUTS)

Typical clinical symptoms included in this group are hesitance, poor urinary stream, terminal drippling and incomplete bladder emptying. The main functional cause of LUTS is urethral sphincter dysfunction. The urethral sphincter consists of a voluntary (striated) sphincter (rhabdosphincter) and an involuntary (smooth) sphincter. The distal part of the male rhabdosphincter surrounds the membranous part of the urethra and is called external sphincter. The upper or prostatic part of the rhabdosphincter is layered out over the anterior and lateral aspects of the prostate and embedded in the prostatic stroma in men. The urethral smooth muscle is located at the bladder neck and prostatic urethra in men. Lowering of resistance of the smooth and striated sphincter, associated with coordinated detrusor contraction determines complete micturition. In urethral sphincter dysfunction an increased intraluminal bladder pressure is needed to empty the bladder. In the initial stages, there is no reduction in the flow rate because the maximum micturition pressure compensates for the increased outflow resistance. The reduction of the flow rate developing in more advanced clinical stages of urethral dysfunction correlates poorly with the degree of prostatic enlargement.

Three different clinical outcomes have been described: 1) bladder neck dyssynergia, 2) external sphincter pseudodyssynergia and 3) Hinman syndrome. They have all been defined as detrusor urethral sphincter dyssynergia.

Bladder neck dyssynergia is defined as the inability of the bladder neck to open properly and assume a funnel shape in the presence of a normal detrusor contraction. Video imaging techniques allow the diagnosis of the smooth sphincter dyssynergia. The bladder neck dyssynergia is a life-long condition, and virtually never occurs in the female. The cause of the bladder neck dyssynergia is unknown.

During the normal micturition cycle, an increase in external sphincter electromyographic activity accompanies bladder filling (continence reflex). This is followed by relaxation of rhabdosphincter and the pelvic floor muscles, which begins before or at the beginning of the detrusor contraction and persists throughout the contraction. Rhabdosphincter dyssynergia is defined as an inappropriate increase in striated urethral muscle (external urethral sphincter) activity during a detrusor contraction and is a well recognized cause of voiding dysfunction in patients with upper neurone lesions. This overcompensation owing to the loss of supraspinal influences is done to counteract the elevated bladder pressure caused by uninhibited detrusor contraction (an exaggerated continence reflex). In external sphincter pseudodyssynergia, incoordination between the bladder and urethral sphincter is not due to a neurological lesion but is secondary to a dysfunction resulting in an increased tone of the external sphincter and the pelvic floor muscles. Pseudodyssynergia is determined by intermittent increase in sphincter EMG and/or intermittent narrowing of the urethra at this site.

Urodynamic investigations in children with an abnormal voiding pattern have shown dyssynergia between the detrusor and striated urethral sphincter in the absence of neurological disease (non-neurogenic neurogenic bladder or the Hinman syndrome). This appears to result from unintentional, habitual contractions of the striated urethral sphincter in response to involuntary bladder contraction to prevent urinary incontinence. This dyssynergia probably may at least partly represent a learned habit. The relationship between the Hinman syndrome and the external sphincter pseudodyssynergia is not known.

Patients with urethral sphincter dysfunction may develop secondary detrusor instability with irritative symptoms of frequency, urgency and nocturia.

LUTS may be associated with chronic pelvic pain. The article written by Oliver W Hakenberg and Manfred P Wirth (Urol Int 2002: 68:138-143), concerns chronic pelvic pain syndrome (CPPS) in men. This is defined as a condition of pelvic pain of more than 6 months duration. Certain conditions causing CPPS are mentioned, namely abacterial prostatitis, stress prostatitis, prostatodynia, urethral syndrome, trigonitis and orchialgia. Interstitial cystitis in men or women will also typically result in pelvic pain. A primary difficulty noted in patients with CPPS is the inability to voluntarily relax the external sphincter and the pelvic floor muscles. This will result in the emergency of LUTS and dyssynergic voiding.

On the basis of the findings in experimental animals (Streng: Hormone-related reversible urinary rhabdosphincter disorder in male laboratory rodents—possible clinical implications. Academic dissertation, University of Turku, 2002), we suggest that the increased ratio of estrogen to androgen concentration (relative overaromatization of androgens) in the organism plays a role in the development of the urethral sphincter dysfunction in men. In male animals chronically treated with estrogen bladder outlet obstruction develops with complete urinary retention and hypertrophy of the bladder wall. Neonatally estrogenized animals have a lower voided urine volume and decreased ratio of urinary flow rate-to-bladder pressure, which are consistent with infravesical obstruction. These urodynamic changes of the neonatally estrogenized animals are reversed after the treatment of aromatase inhibitor in adulthood. The urethral smooth and striated sphincters and neurones innervating them show androgen and estrogen receptors suggesting that they are the potential target of androgens and estrogen actions. The prostate of these animals have reduced size and show signs of inflammation.

U.S. Pat. No. 5,972,921 describes a method for the treatment of detrusor urethral sphincter dyssynergia in men by administering an aromatase inhibitor to the patient. Said patent gives a summary of the clinical symptoms of male functional detrusor urethral sphincter dyssynergia and its treatments taking into account especially the possible hormonal background of the symptoms. Aromatase inhibitors, when studied in men with urinary symptoms (A Radlmaier et al., The Prostate 29:199-208 (1996); J C Gingell et al., The Journal of Urology, vol. 154,399-401, August 1995), increase the concentrations of testosterone. This causes an increase in the size of prostate and on the other hand may worsen the static obstruction caused by the enlarged prostate and consequently the symptoms. Therefore, other mechanisms of action are desirable. SERMs, which act as antiestrogens in the urinary tract, decrease the detrimental effect of natural estrogens without stimulating the prostate size. They can be considered as potentially beneficial compounds in treating the symptoms and functional causes of LUTS.

Selective Estrogen Receptor Modulators

"SERMs" (selective estrogen receptor modulators) have both estrogen-like and antiestrogenic properties (Kauffman & Bryant, Drug News Perspect 8:531-539, 1995). The effects may be tissue-specific as in the case of tamoxifen and toremifene which have estrogen-like effects in the bone, partial estrogen-like effect in the uterus and liver, and pure antiestrogenic effect in breast cancer. Raloxifene and droloxifen are similar to tamoxifen and toremifene, except that their antiestrogenic properties dominate. They are known to decrease total and LDL cholesterol, thus diminishing the risk of cardiovascular diseases, and they may prevent osteoporosis and inhibit breast cancer growth in postmenopausal women. There are also almost pure antiestrogens under development. They are mainly aimed at the treatment of breast cancer (Wakeling & Bowler, J Steroid Biochem 30:1-6, 1988).

A review of investigated and/or marketed SERM compounds is published in V Craig Jordan, J Medicinal Chemistry (2003):46, No. 7.

SUMMARY OF THE INVENTION

The inventors of the present invention have surprisingly found that compounds belonging to the group of selective estrogen receptor modulators have beneficial effects on urodynamic parameters in animal studies. Therefore, the inventors suggest that this class of compounds may be useful for treating or preventing LUTS caused by urethral sphincter dysfunction.

Thus, this invention concerns a method for treatment or prevention of lower urinary tract symptoms with or without pelvic pain in an individual, said method comprising administering to the individual an effective amount of a selective estrogen receptor modulator, or an isomer, isomer mixture or a pharmaceutically acceptable salt thereof.

DETAILED DESCRIPTION OF THE INVENTION

Definitions

The term "individual" relates particularly to humans, but it shall also be considered to include animals.

The term "lower urinary tract symptoms" relates to symptoms in male as well as in female individuals. For male individuals, a particularly important class of such symptoms is detrusor urethral sphincter dyssynergia, but the term is not restricted hereto. Any kind of symptoms in the lower urinary tract in male individuals shall be covered by the term. Thus, in this invention the term "lower urinary tract symptoms" shall also be understood to include abacterial prostatitis, stress prostatitis, trigonitis and orchialgia in male individuals, and interstitial cystitis in male or female individuals. For female individuals, this term further include bladder instability and micturition urgency.

The term "pelvic pain" shall here be understood to include symptoms related to abacterial prostatitis, stress prostatitis, prostatodynia, urethral syndromes, trigonitis or orchialgia in a male individual. Furthermore, the term includes interstitial cystitis either in male or female individuals.

The wording "selective estrogen receptor modulator" and any specific compound belonging to this group shall be understood to cover any geometric isomer, any stereoisomer, racemate or other mixture of isomers of the compound. Furthermore, pharmaceutically acceptable salts and other derivatives such as esters are also included.

Suitable selective estrogen receptor modulators (or SERMs) for use in this invention are, for example, the compounds disclosed in V Craig Jordan (2003).

Thus, examples of suitable SERM compounds for use in the present invention are triphenylalkene or triphenylalkane compounds such as compounds disclosed in WO 01/36360, U.S. Pat. No. 4,996,225, U.S. Pat. No. 4,696,949, U.S. Pat. No. 5,750,576, WO 99/42427 and the toremifene metabolites disclosed in L Kangas, Cancer Chemother Pharmacol (1990) 27:8-12. As examples of specific drugs disclosed in the aforementioned references can be mentioned toremifene, ospemifene and ospemifene. Tamoxifen and its derivatives such as 4-hydroxytamoxifen, alpha-hydroxytamoxifen, N-desmethyltamoxifen, N,N-didesmethyltamoxifen, deaminotamoxifen, and droloxifene and iodoxifene also examples of suitable SERMs of triphenylalkene structure.

Other preferable examples of SERM compounds are compounds of benzothiophene structure, such as raloxifene and its analogues (described for example in EP 584952, U.S. Pat. No. 4,133,814, U.S. Pat. No. 4,418,068) and arzoxifene.

As further examples of suitable SERMs can be mentioned EM652, EM800, EM776, EM651, EM312, ICI 182780, ERA-923, zindoxifene and deacetylated zindoxifene, ZK119010, TSE-4247, lasoxifene and its analogues, particularly those disclosed in EP 802910, nafoxidine, basedoxifene, GW5638, GW7604, compound no. 32 disclosed in Jordan (2003), ICI 164384, RU 58668, RU 39411 and EM 319.

The aforementioned specific SERMs or classes of SERMs are examples only, and other SERMs may be suitable for use in this invention as well.

SERMs with no or weak estrogenic effect may be suitable for use, particularly in male individuals. A classical method to determine the estrogenic profile of a compound is to evaluate estrogenic effect in immature mouse or rat uterus (Terenius L, Acta Endocrinol 66:431-447, 1971). The animals are exposed for 3 days to the compounds to be investigated at the age of 18 days. On the fourth day the animals are sacrificed and body weight and uterine weight is recorded. Estrogens increase the size and weight of the uterus (uterotropic effect) while anti-estrogens inhibit this action. The results are given as per cent of estrogen stimulation (100% with estradiol). In our tests, we used a high dose level, i.e. 10-50 mg/kg. Compounds causing an uterotropic effect≤40% are for this purpose classified as weak estrogenic compounds, compounds causing an uterotropic effect≥70% are classified as strong estrogenic compounds and compounds in-between, an uterotropic effect of 41-69% are classified as moderate estrogenic agents.

As specific examples of particularly useful SERMs can be mentioned certain compounds of those disclosed in WO 01/36360 (incorporated herein by reference), namely (Z)-2-[3-(4-Chloro-1,2-diphenyl-but-1-enyl)phenoxy]ethanol (Z)-2-{2-[4-(4-Chloro-1,2-diphenylbut-1-enyl)phenoxy]ethoxy}ethanol (also known under the generic name fispemifene)

(Z)-{2-[3-(4-Chloro-1,2-diphenylbut-1-enyl)phenoxy]ethyl}dimethylamine (E)-3-{4-Chloro-1-[4-(2-hydroxyethoxy)phenyl]-2-phenyl-but-1-enyl}-phenol (E)-3-{4-Chloro-1-[4-(2-imidazol-1-yl-ethoxy)phenyl]-2-phenyl-but-1-enyl}-phenol, and (Z)-3 (Z)-3-{4-Chloro-1-[4-(2-imidazol-1-yl-ethoxy)phenyl]-2-phenyl-but-1-enyl}-phenol.

The aforementioned six compounds are all classified as weak estrogenic SERMs.

For the purpose of this invention, the SERM or its isomer, isomer mixture or their pharmaceutically acceptable salts can be administered by various routes. The suitable administration forms include, for example, oral formulations; parenteral injections including intravenous, intramuscular, intradermal and subcutaneous injections; and transdermal or rectal formulations. Suitable oral formulations include e.g. conventional or slow-release tablets and gelatine capsules.

The required dosage of the SERM compounds will vary with the particular condition being treated, the severity of the condition, the duration of the treatment, the administration route and the specific compound being employed. For example, fispemifene can be administered perorally preferentially once daily. The daily dose may be 5-150 mg, preferably 20-100 mg. Fispemifene can be given as tablets or other formulations like gelatine capsules alone or mixed in any clinically acceptable non-active ingredients which are used in the pharmaceutical industry.

The invention will be illuminated by the following non-restrictive Experimental Section.

EXPERIMENTAL SECTION

Methods and Materials

Tested Drugs:

We studied the effects of two SERMs, namely fispemifene, which also is known under the code HM-101, and raloxifene on voiding in control as well as in developmentally estrogenized male rats. As vehicle was used polyethylene glycol (PEG).

Animals:

Male rats were supplied by The Central Animal Laboratory of the University of Turku, Finland. Their mean age was 222 days (SD 48.4). The number of the non-estrogenized rats was 50 and the number of developmentally estrogenized rats was 29. The rats were maintained under standard laboratory conditions at 12:12 light/dark cycle and they got soyfree pelleted food (SDS, Witham, Essex, UK) with free access. They had also free access to tap water.

The estrogenized rats (neoDES) were developed as follows: Male Noble rats were treated neonatally with estrogen (10 μg of diethylstilbestrol (DES)) in rap seed oil (10 μg/40 μl) s.c. on days 1-5 of postnatal life. After the treatment with diethylstilbestrol, the neoDES rats were left to grow for 4-5 months before treatment with study drugs.

Dosing and Weighing:

The dosing volume was 0.2 ml solutions/50 g body weight and the dose level of fispemifene or raloxifene 1 and/or 10 mg/kg body weight. The dose was given once a day for six weeks. The rats were weighed for the first time on the same day, as the treatments began. Afterwards the animals were weighed once a week. This was carried out to ensure the right dosing to rats.

Study Design for Urodynamic Studies:

There were eight groups of adult male rats. The anesthetized rats (non-estrogenized or neonatally estrogenized) were treated orally with fispemifene or raloxifene using doses of 1 and/or 10 mg/kg body weight.

The following animal codes are used in the study:

Treatment of Non-Estrogenized Rats:

| Control rats (only with vehicle treatment) | Co |
|---|---|
| Rats treated with fispemifene, 1 mg/kg dose | HMCo1 |
| Rats treated with fispemifene, 10 mg/kg dose | HMCo10 |
| Rats treated with raloxifene, 1 mg/kg dose | RalCo1 |
| Rats treated with raloxifene, 10 mg/kg dose | RalCo10 |

Treatment of Neonatally Estrogenized Rats:

| Control rats (neoDES) (only with vehicle treatment) | neoDES |
|---|---|
| Rats treated with fispemifene, 10 mg/kg dose | HMDES10 |
| Rats treated with raloxifene, 10 mg/kg dose | RalDES10 |

The above codes are used in the tables and figures.

Measurements and Apparatus:

The rats were anesthetized with chloral hydrate (0.9 g/kg, Sigma Chemical Co. St. Louis. Mo. 63178, USA) for a basic anesthetic, and i.v. injection of urethane (0.32 g/kg, Sigma Chemical Co. St. Louis. Mo. 63178, USA) was used to maintain anesthesia for urodynamic measurements. The body temperature was kept constant at +36-38° C. by a thermostatically controlled animal blanket and if needed, with a heating lamp. The bladder and the distal part of urethra were exposed with a midline incision of the lower abdomen. In transvesical cystometry a 20 G i.v. cannula was inserted through the bladder apex into the lumen. The cannula was connected to an infusion pump and to a pressure transducer. The whole system was filled with saline. Measurements were made at the infusion rate of 0.23 ml/min. An ultrasonic flow probe was used for measurement of the flow rate from the distal part of urethra. The flow probe was connected to a flow meter, with sampling rate of 100 Hz. At the same time with the measurements of transvesical cystometry and flow rate, the electrical activity of the striated urethral sphincter (rhabdosphincter) was measured extracellularly with suction electrode. The electrode was attached on anterior surface of the muscle by suction (provided by a flow of tap water). The suction electrode and pressure transducer were connected to an amplifier. Low frequency AC coupling (0.8 Hz) was used in electrical activity measurement. The reference and ground electrodes were placed on the edge of the wound so that ECG signal was not observable. The tissues were kept moist during measurements with warm (+37° C.) saline. The pressure and flow meter signals were transferred to the Biopac-system. The Biopac-system was connected to a personal computer. Continuous recording was made with Acq Knowledge 3.5.3 program with sample rate of 400 Hz.

The setup of the apparatus for use in this method is disclosed in U.S. Pat. No. 5,972,921 (column 9-10, FIG. 3).

Three representative voidings were chosen for further analysis from each rat. Intraluminal pressure high frequency oscillations (IPHFOs) of bladder pressure are characteristic in male rodent micturition during the second phase, during which also the urine flow occurs. The maximum and mean bladder pressures were calculated from the pressure oscillations seen in pressure wave. The maximum value was measured from the highest peak and the mean value from all IPHFOs during the second phase of micturition. The maximum flow rate value was measured from the highest flow rate peak and the mean flow rate value from all flow peaks during the second phase of micturition. The duration of the micturition and the volume of the residual urine were measured.

Figure 1:
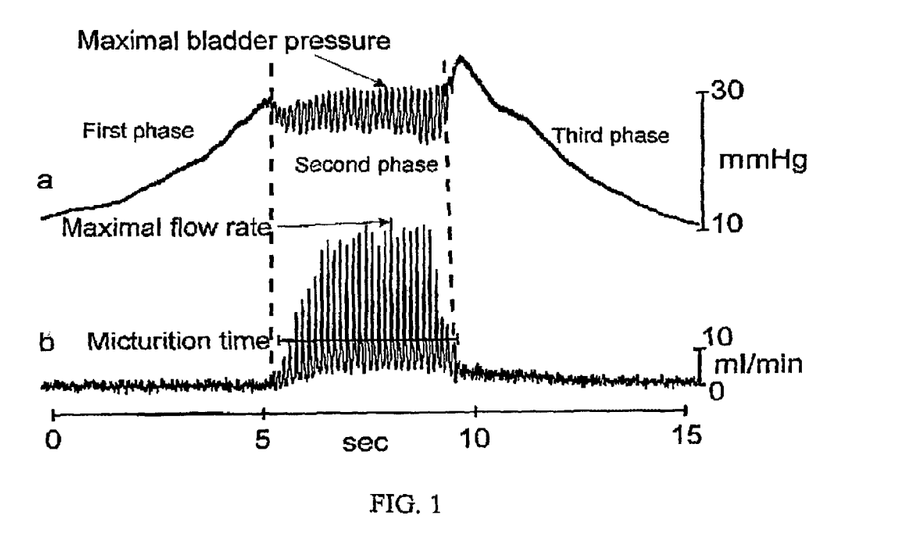
FIG. 1 shows a typical micturition cycle (a=bladder pressure; b=flow rate).

FIG. 1 illustrates one typical micturition cycle showing bladder pressure wave (a) and flow rate wave (b), and the method for calculation of the urodynamic parameters. The measurement of the maximal bladder pressure, flow rate, and micturition time are shown in the figure. Parameters of mean bladder pressure and flow rate are measured as average from all the bladder pressure and flow rate peaks, respectively.

Statistics

Continuous recording was made by Acq Knowledge 3.5.3 program (MP100 Manager Ver. 3.5.3, Copyright© 1992-95 BIOPAC Systems Inc.). Further numerical data were carried out with Excel 2000 (Microsoft Corporation, Redmond, Wash., USA), and the statistical analysis with Statistica for Windows 5.1 (Stat Soft, Inc., Tulsa, Okla., USA). Statistical analysis was carried out with ANOVA and the post hoc tests with HSD test. If Levene's test for variances shows significant differences ($p<0.05$) between the treatment groups, Kruskall-Wallis test was be used, and Mann-Whitney U test was used as a post hoc test.

Results

Bladder Pressure

There were no significant differences in the bladder pressures (maximal and mean) between the groups (Tables 1 and 2). Because neoDES treatment did not influence on the bladder pressure, it is not expected that SERMs would influence on it either.

TABLE 1

Maximal bladder pressure (MBP) (measured from highest bladder pressure oscillation). M = Mann-Whitney U test.

| Animal group and treatment | MBP Mean (mmHg) | SD | P-value Co compared to neoDES and Co rat treatments, and neoDES compared to HMDES10 and RalDES10 |
|---|---|---|---|
| Co, (n = 10) | 35.5 | 2.73 | |
| HMCo1, (n = 10) | 38.2 | 6.06 | 0.13 (M) |
| HMCo10, (n = 10) | 35.1 | 2.01 | 0.36 (M) |

TABLE 1-continued

Maximal bladder pressure (MBP) (measured from highest bladder pressure oscillation). M = Mann-Whitney U test.

| Animal group and treatment | MBP Mean (mmHg) | SD | P-value Co compared to neoDES and Co rat treatments, and neoDES compared to HMDES10 and RalDES10 |
|---|---|---|---|
| RalCo1, (n = 10) | 36.9 | 6.12 | 0.71 (M) |
| RalCo10, (n = 10) | 39.4 | 8.49 | 0.29 (M) |
| neoDES, (n = 9) | 34.4 | 6.43 | 0.22 (M) |
| HMDES10, (n = 10) | 38.2 | 7.97 | 0.32 (M) |
| RalDES10, (n = 8) | 35.9 | 8.41 | 0.92 (M) |

TABLE 2

Mean bladder pressure (MeBP) (measured from all bladder pressure oscillations). A = One Way ANOVA and Tukey HSD test; M = Mann-Whitney U test.

| Animal group and treatment | MeBP Mean (mmHg) | SD | P-value Co compared to neoDES and Co rat treatments, and neoDES compared to HMDES10 and RalDES10 |
|---|---|---|---|
| Co, (n = 10) | 26.0 | 2.14 | |
| HMCo1, (n = 10) | 25.8 | 3.77 | 0.99 (A) |
| HMCo10, (n = 10) | 24.4 | 2.89 | 0.85 (A) |
| RalCo1, (n = 10) | 26.7 | 3.73 | 0.99 (A) |
| RalCo10, (n = 10) | 25.8 | 4.12 | 0.99 (A) |
| neoDES, (n = 9) | 24.8 | 3.69 | 0.97 (M) |
| HMDES10, (n = 8) | 25.6 | 5.67 | 1.00 (M) |
| RalDES10, (n = 8) | 24.1 | 3.16 | 0.44 (M) |

Figure 2:
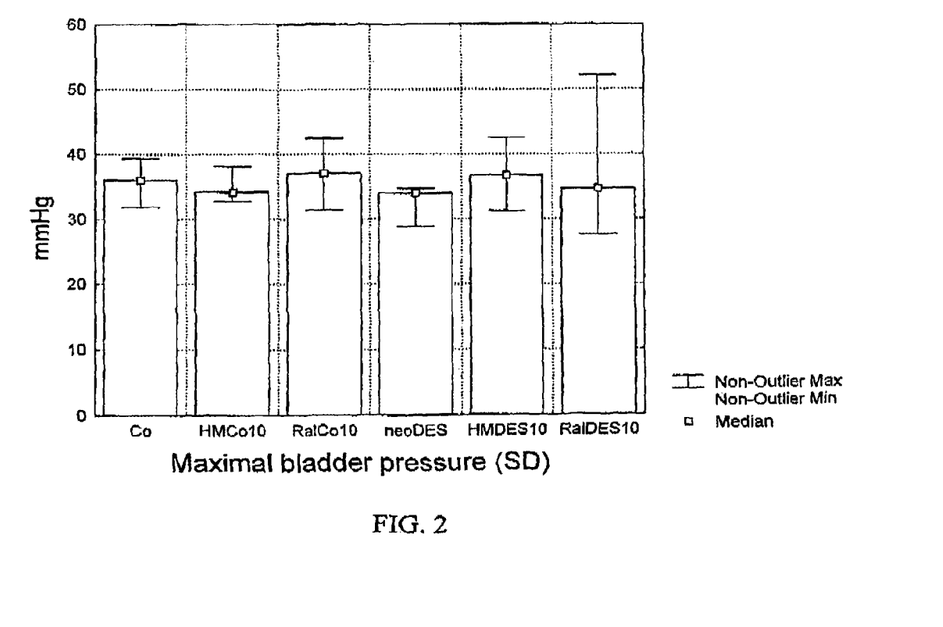
FIG. 2 shows the maximal bladder pressure for non-estrogenized rats and for neoDES rats with and without administration of test compounds.
Figure 3:
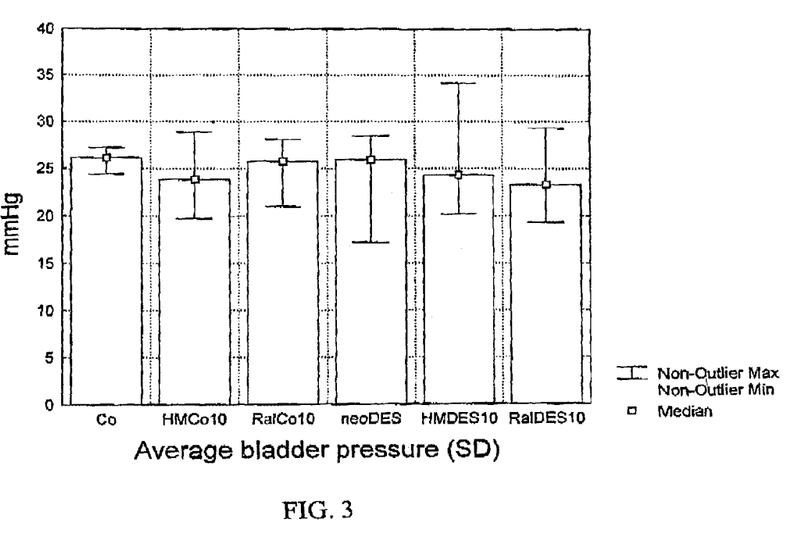
FIG. 3 shows the average bladder pressure for non-estrogenized rats and for neoDES rats with and without administration of test compounds.

The maximal and average bladder pressures are also shown in FIGS. 2 and 3.

Flow Rate

Decreased urine flow rate is a definite sign of urination problems. NeoDES treatment decreased the flow rate and SERMs normalized it indicating a positive effect on urodynamics. Treatment with fispemifene or raloxifene increased both the maximal (Table 3) and mean (Table 4) flow rate in non- and neonatally estrogenized rats with dose of 10 mg/kg. No differences were seen with dose of 1 mg/kg in non-estrogenized rats. Neonatally estrogenized rats received only 10 mg/kg of drug treatment. Neonatally estrogenized rats showed lower flow rates than non-estrogenized rats.

TABLE 3

Maximal flow rate (MFR) (measured from highest flow rate peak). A = One Way ANOVA and Tukey HSD test; M = Mann-Whitney U test.

| Animal group and treatment | MFR Mean (ml/min) | SD | P-value Co compared to neoDES and Co rat treatments, and neoDES compared to HMDES10 and RalDES10 |
|---|---|---|---|
| Co, (n = 10) | 34.0 | 11.95 | |
| HMCo1, (n = 10) | 40.9 | 20.90 | 0.90 (A) |
| HMCo10, (n = 10) | 55.8 | 20.13 | 0.053 (A) |
| RalCo1, (n = 10) | 40.1 | 13.32 | 0.93 (A) |
| RalCo10, (n = 10) | 67.1 | 18.39 | 0.001 (A) |
| neoDES, (n = 9) | 24.8 | 6.80 | 0.07 (A) |
| HMDES10, (n = 10) | 40.9 | 15.14 | 0.007 (M) |
| RalDES10, (n = 8) | 45.9 | 20.66 | 0.03 (M) |

TABLE 4

Mean flow rate (MeFR) (measured from all flow rate peaks).
M = Mann-Whitney U test.

| Animal group and treatment | MeFR Mean (ml/min) | SD | P-value Co compared to neoDES and Co rat treatments, and neoDES compared to HMDES10 and RalDES10 |
|---|---|---|---|
| Co, (n = 10) | 4.9 | 1.64 | |
| HMCo1, (n = 10) | 6.5 | 3.63 | 0.50 (M) |
| HMCo10, (n = 10) | 8.4 | 4.38 | 0.03 (M) |
| RalCo1, (n = 10) | 5.8 | 1.95 | 0.26 (M) |
| RalCo10, (n = 10) | 8.3 | 2.81 | 0.008 (M) |
| neoDES, (n = 9) | 3.3 | 1.19 | 0.03 (M) |
| HMDES10, (n = 10) | 5.8 | 2.12 | 0.009 (M) |
| RalDES10, (n = 8) | 6.3 | 3.72 | 0.02 (M) |

Figure 4:
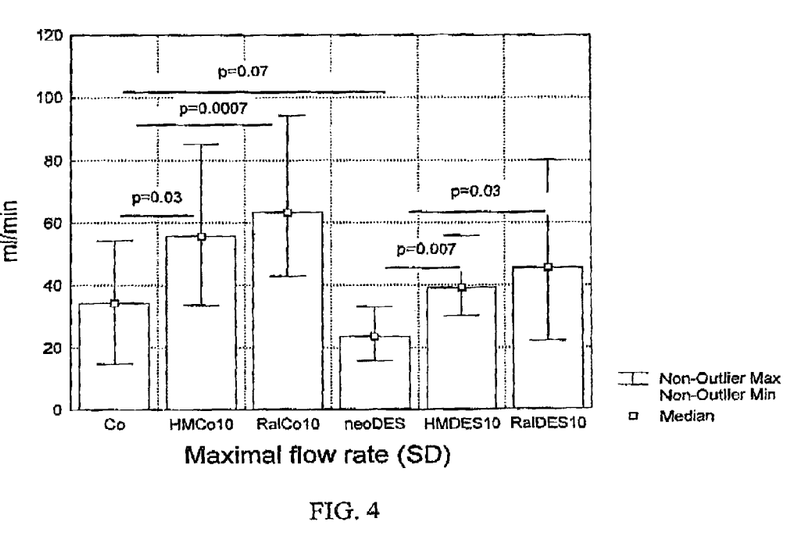
FIG. 4 shows the maximal flow rate for non-estrogenized rats and for neoDES rats with and without administration of test compounds.
Figure 5:
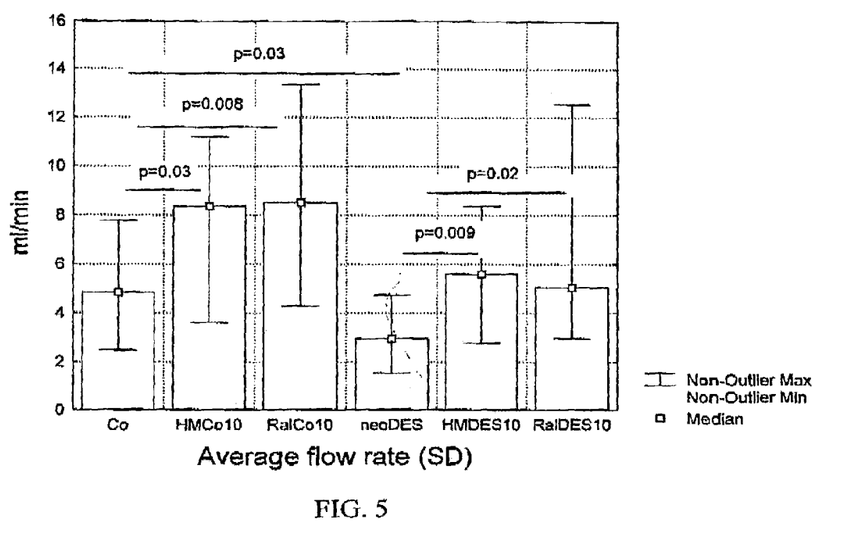
FIG. 5 shows the average flow rate for non-estrogenized rats and for neoDES rats with and without administration of test compounds.

The maximal and mean flow rates are also shown in FIGS. 4 and 5.

Micturition Time

Micturition time was significantly prolonged in neonatally estrogenized rats (Table 5). This is well understandable, because the urine flow rate was decreased. Treatments with HM-101 or raloxifene did not shorten the micturition time in non-estrogenized rats. In neonatally estrogenized rats the treatments shortened the micturition time. Although the effect did not quite reach the statistical significance, the effect can be considered beneficial.

TABLE 5

Micturition time (MT; the time from the first flow peak to last one).
M = Mann-Whitney U test.

| Animal group and treatment | MT Mean (sec) | SD | P-value Co compared to neoDES and Co rat treatments, and neoDES compared to HMDES10 and RalDES10 |
|---|---|---|---|
| Co, (n = 10) | 7.8 | 2.10 | |
| HMCo1, (n = 10) | 6.6 | 1.75 | 0.29 (M) |
| HMCo10, (n = 10) | 6.6 | 2.93 | 0.20 (M) |
| RalCo1, (n = 10) | 7.4 | 2.27 | 0.45 (M) |
| RalCo10, (n = 10) | 7.5 | 1.62 | 0.82 (M) |
| neoDES, (n = 9) | 19.1 | 6.97 | 0.001 (M) |
| HMDES10, (n = 10) | 13.1 | 7.16 | 0.07 (M) |
| RalDES10, (n = 8) | 13.4 | 7.03 | 0.054 (M) |

Figure 6:
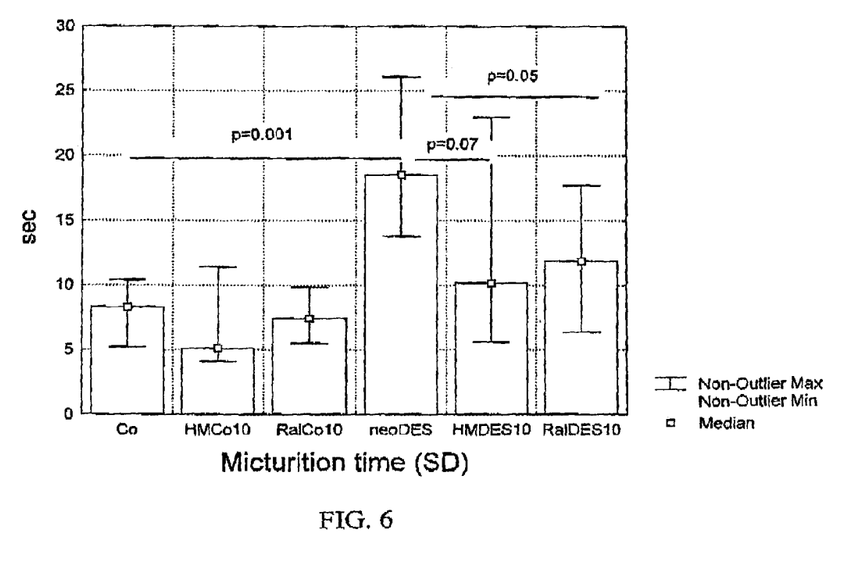
FIG. 6 shows the micturition time for non-estrogenized rats and for neoDES rats with and without administration of test compounds.

The micturition time is also shown in FIG. 6.

Residual Urine

The amount of residual urine was increased significantly in neonatally estrogenized rats indicating that the bladder was not completely empty after urination. Residual urine leads to increased urination frequency and is also a risk factor of lower urinary tract infections. The treatment with fispemifene (10 mg/kg) did reduce the amount of residual urine both in non- and neonatally estrogenized rats. This result is very promising and indicates improved functional activity of the bladder. Raloxifene (10 mg/kg) reduced the amount of residual urine almost significantly in non-estrogenized, and significantly in neonatally estrogenized rats (Table 6).

TABLE 6

Residual urine (RU). M = Mann-Whitney U test.

| Animal group and treatment | RU Mean (ml) | SD | P-value Co compared to neoDES and Co rat treatments, and neoDES compared to HMDES10 and RalDES10 |
|---|---|---|---|
| Co, (n = 10) | 0.58 | 0.192 | |
| HMCo10, (n = 10) | 0.35 | 0.182 | 0.02 (M) |
| RalCo10, (n = 10) | 0.42 | 0.139 | 0.07 (M) |
| neoDES, (n = 9) | 1.31 | 0.620 | 0.009 (M) |
| HMDES10, (n = 10) | 0.63 | 0.507 | 0.04 (M) |
| RalDES10, (n = 8) | 0.64 | 0.202 | 0.02 (M) |

Figure 7:
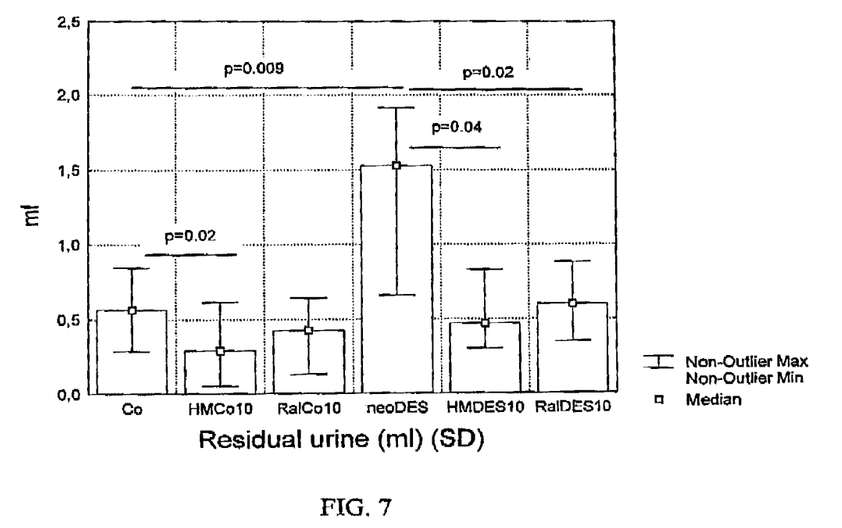
FIG. 7 shows the amount of residual urine for non-estrogenized rats and for neoDES rats with and without administration of test compounds.

The residual urine is also shown in FIG. 7.

Bladder Capacity

Bladder capacity was increased significantly in neonatally estrogenized rats. Although the increased bladder capacity can be considered beneficial as such, the increase in neoDES rats indicates abnormal relaxation of bladder wall muscles and thus damage of the bladder (due to residual urine and slow urine flow). The bladder tries to compensate the increased need of bladder volume. However, in such conditions the bladder wall looses its strength. Treatment with fispemifene (10 mg/kg) reduced significantly the bladder capacity in neonatally estrogenized rats, and raloxifene almost significantly indicating that the bladder wall has retained its normal strength and function. This effect can be considered very beneficial. No effects were seen in non-estrogenized rats (Table 7). This is expected, as the bladder in these animals is not damaged.

TABLE 7

Bladder capacity (BC). M = Mann-Whitney U test.

| Animal group and treatment | BC Mean (ml) | SD | P-value Co compared to neoDES and Co rat treatments, and neoDES compared to HMDES10 and RalDES10 |
|---|---|---|---|
| Co, (n = 10) | 0.88 | 0.210 | |
| HMCo10, (n = 10) | 0.79 | 0.191 | 0.41 (M) |
| RalCo10, (n = 10) | 0.81 | 0.206 | 0.45 (M) |
| neoDES, (n = 9) | 1.678 | 0.468 | 0.001 (M) |
| HMDES10, (n = 10) | 1.21 | 0.486 | 0.04 (M) |
| RalDES10, (n = 8) | 1.22 | 0.285 | 0.054 (M) |

Figure 8:
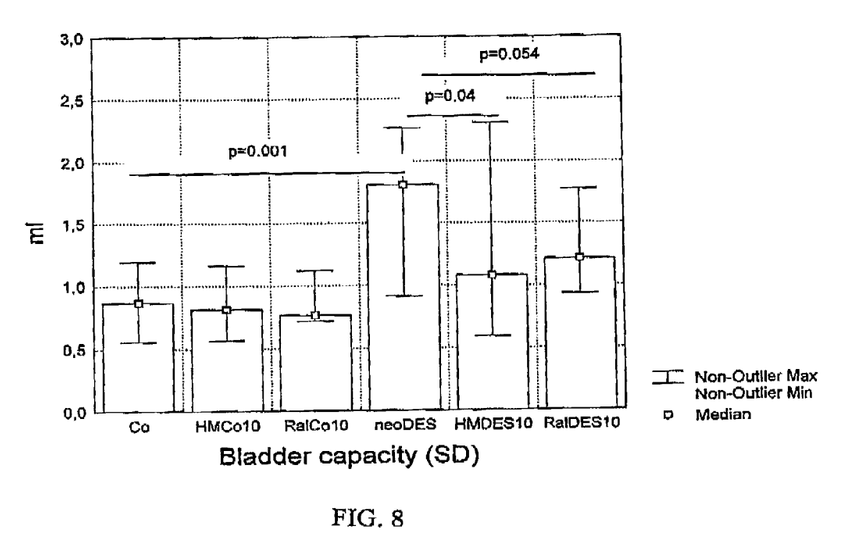
FIG. 8 shows the bladder capacity for non-estrogenized rats and for neoDES rats with and without administration of test compounds.

The bladder capacity is also illustrated in FIG. 8.

Discussion and Conclusions

Treatments with SERMs (fispemifene or raloxifene) had similar effects in non- and neonatally estrogenized rats. They had increased maximum and mean flow rates. Duration of micturition consisting of multiple voidings in neonatally estrogenized rats was shortened, while no differences were seen in bladder pressures between the groups. Amount of residual urine was reduced both in non- and neonatally estrogenized rats, which indicates improvement of bladder function even in the non-estrogenized rats as well as the increase in flow rates does. It is known that estrogenization of the rodents increases the bladder capacity. This was evident also in present study. The treatments with these SERMs decreased the bladder capacity in neonatally estrogenized rats. Thus the studied SERMs had antiestrogen function on bladder capacity. The rhabdosphincter function was improved in both non- and neonatally estrogenized rats, but the EMG changes were not statistically significant.

Fispemifene and raloxifene reversed the estrogen-related alterations in flow rates, micturition time, and bladder capacity (fispemifene even in non-estrogenized rats).

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A method for treatment of obstructive lower urinary tract symptoms in a male individual, said method comprising administering to the individual an effective amount of (Z)-2-{2-[4-(4-Chloro-1,2-diphenylbut-1-enyl)phenoxy]ethoxy}ethanol (fispemifene), or an isomer, isomer mixture or a pharmaceutically acceptable salt thereof, wherein the obstructive lower urinary tract symptoms are caused by detrusor urethral sphincter dyssynergia.

2. The method according to claim 1, wherein the detrusor urethral sphincter dyssynergia comprises bladder neck dyssynergia, external sphincter pseudodyssynergia, or Hinman syndrome.

3. The method according to claim 1, wherein the obstructive lower urinary tract symptoms comprise hesitance, poor urinary stream, terminal dripping, or incomplete bladder emptying.

4. The method according to claim 2, wherein the obstructive lower urinary tract symptoms comprise hesitance, poor urinary stream, terminal dripping, or incomplete bladder emptying.

5. The method according to claim 1, wherein the method comprises administering to the individual an effective amount of fispemifene.

6. The method according to claim 2, wherein the method comprises administering to the individual an effective amount of fispemifene.

7. The method according to claim 3, wherein the method comprises administering to the individual an effective amount of fispemifene.

8. The method according to claim 4, wherein the method comprises administering to the individual an effective amount of fispemifene.

* * * * *